United States Patent
Coniglione

(10) Patent No.: US 6,347,443 B2
(45) Date of Patent: Feb. 19, 2002

(54) METHOD OF MAKING A HOLLOW-TUBE PRECURSOR BRACHYTHERAPY DEVICE

(75) Inventor: Roy Coniglione, Louvain-la-Neuve (BE)

(73) Assignee: International Brachytherapy S.A., Seneffe (BE)

( * ) Notice: Subject to any disclaimer, the term of this patent is extended or adjusted under 35 U.S.C. 154(b) by 0 days.

(21) Appl. No.: 09/747,800

(22) Filed: Dec. 22, 2000

Related U.S. Application Data

(62) Division of application No. 08/903,850, filed on Jul. 31, 1997, now Pat. No. 6,163,947, which is a continuation-in-part of application No. 08/563,050, filed on Nov. 27, 1995, now Pat. No. 5,713,828, which is a continuation of application No. PCT/US96/19109, filed on Nov. 25, 1996.

(51) Int. Cl.⁷ ................................................. B23P 15/00
(52) U.S. Cl. ....................................... 29/401.1; 29/527.1
(58) Field of Search ............................ 29/401.1, 527.1, 29/428, 458, 527.25; 600/7, 3

(56) References Cited

U.S. PATENT DOCUMENTS

| | | | |
|---|---|---|---|
| 839,061 A | 12/1906 | Farjas | |
| 1,603,767 A | 10/1926 | Harris | |
| 1,753,287 A | 4/1930 | Failla | |
| 1,754,178 A | 4/1930 | Muir | |
| 1,954,868 A | 4/1934 | Failla et al. | 174/177 |
| 2,153,889 A | 4/1939 | Hames | 128/1 |
| 2,429,438 A | 10/1947 | Wappler | 128/1 |
| 2,546,761 A | 3/1951 | Loftus | 128/1 |
| 2,917,041 A | 12/1959 | Becker et al. | 128/1 |
| 3,351,049 A | 11/1967 | Lawrence | 128/1 |
| 3,505,991 A | 4/1970 | Hellerstein et al. | 128/1 |
| 3,674,006 A | 7/1972 | Holmer | 128/1 |
| 3,811,426 A | 5/1974 | Culver et al. | 128/355 |
| 3,872,856 A | 3/1975 | Clayton | 128/1 |
| 3,927,325 A * | 12/1975 | Hungate et al. | |
| 4,096,862 A | 6/1978 | DeLuca | 128/348 |
| 4,323,055 A | 4/1982 | Kubiatowicz | 128/1 |
| 4,510,924 A | 4/1985 | Gray | 128/1 |
| 4,697,575 A | 10/1987 | Horowitz | 128/1 |
| 4,702,228 A | 10/1987 | Russell et al. | 128/1 |
| 4,706,652 A | 11/1987 | Horowitz | 128/1 |
| 4,754,745 A | 7/1988 | Horowitz | 128/1 |
| 4,763,642 A | 8/1988 | Horowitz | 128/1 |
| 4,784,116 A | 11/1988 | Russell | 128/1 |
| 4,789,501 A | 12/1988 | Day et al. | 252/645 |
| 4,815,449 A | 3/1989 | Horowitz | 600/7 |
| 4,819,618 A | 4/1989 | Liprie | 600/7 |
| 4,861,520 A | 8/1989 | Van't Hooft et al. | 252/644 |
| 4,889,707 A | 12/1989 | Day et al. | 424/1 |
| 4,891,165 A | 1/1990 | Suthanthiran | 252/633 |
| 4,921,327 A | 5/1990 | Zito | 350/96 |
| 4,994,013 A | 2/1991 | Suthanthiran | 600/8 |
| 5,011,677 A | 4/1991 | Day et al. | 424/1 |
| 5,011,797 A | 4/1991 | Day et al. | 501/33 |
| 5,030,194 A | 7/1991 | Van't Hooft et al. | 600/3 |
| 5,030,195 A | 7/1991 | Nardi | 600/7 |
| 5,059,166 A | 10/1991 | Fischell et al. | 600/3 |
| 5,084,002 A | 1/1992 | Liprie | 600/7 |
| 5,092,834 A | 3/1992 | Bradshaw et al. | 600/7 |
| 5,106,360 A | 4/1992 | Ishiwara et al. | 600/2 |

(List continued on next page.)

*Primary Examiner*—I Cuda Rosenbaum
(74) *Attorney, Agent, or Firm*—Gerry J. Elman; Elman & Associates

(57) ABSTRACT

A method of making a sealed double-walled tubular precursor device that is adapted to be transmuted into a brachytherapy device is disclosed. The device is hollow-tube-shaped, allowing the easy association of the device with suture material. Disclosed are methods of making devices that can be rendered radioactive by the transmuting effects of irradiation by a cyclotron or nuclear reactor. The brachytherapy devices facilitate medical application and improve safety for patients and medical personnel.

19 Claims, 4 Drawing Sheets

U.S. PATENT DOCUMENTS

| | | | |
|---|---|---|---|
| 5,141,487 A | 8/1992 | Liprie | 600/7 |
| 5,147,282 A | 9/1992 | Kan | 600/1 |
| 5,163,896 A | 11/1992 | Suthanthiran | 600/8 |
| 5,176,617 A | 1/1993 | Fischell et al. | 600/3 |
| 5,183,455 A | 2/1993 | Hayman et al. | 600/7 |
| 5,199,939 A | 4/1993 | Dake | 600/3 |
| 5,213,561 A | 5/1993 | Weinstein et al. | 600/7 |
| 5,282,781 A | 2/1994 | Liprie | 600/3 |
| 5,302,168 A | 4/1994 | Hess | 600/3 |
| 5,322,499 A | 6/1994 | Liprie | 600/8 |
| 5,342,283 A | 8/1994 | Good | 600/8 |
| 5,354,257 A | 10/1994 | Roubin | 600/7 |
| 5,364,366 A | 11/1994 | Carr | 600/2 |
| 5,395,300 A | 3/1995 | Liprie | 600/3 |
| 5,405,309 A * | 4/1995 | Carden, Jr. | |
| 5,460,592 A | 10/1995 | Langton et al. | 600/7 |
| 5,484,384 A | 1/1996 | Fearnot | 600/3 |
| 5,498,227 A | 3/1996 | Mawad | 600/3 |
| 5,503,613 A | 4/1996 | Weinberger | 600/3 |
| 5,503,614 A | 4/1996 | Liprie | 600/7 |

\* cited by examiner

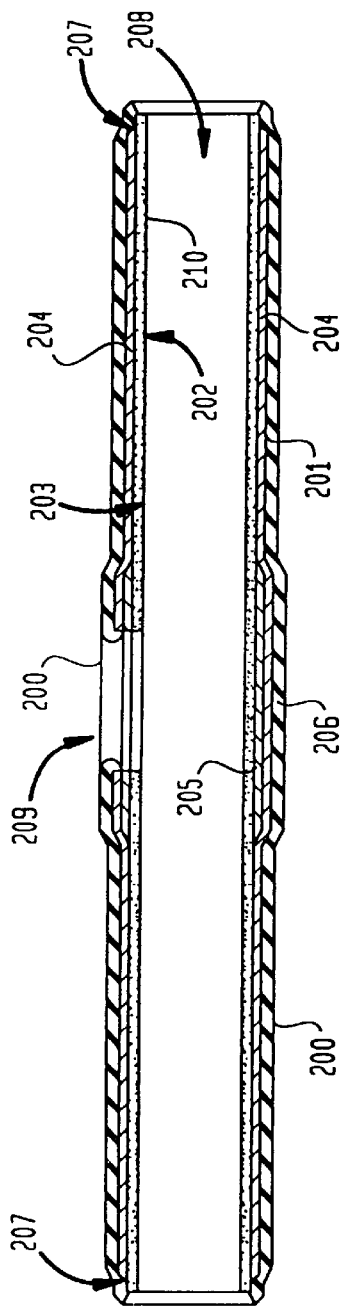
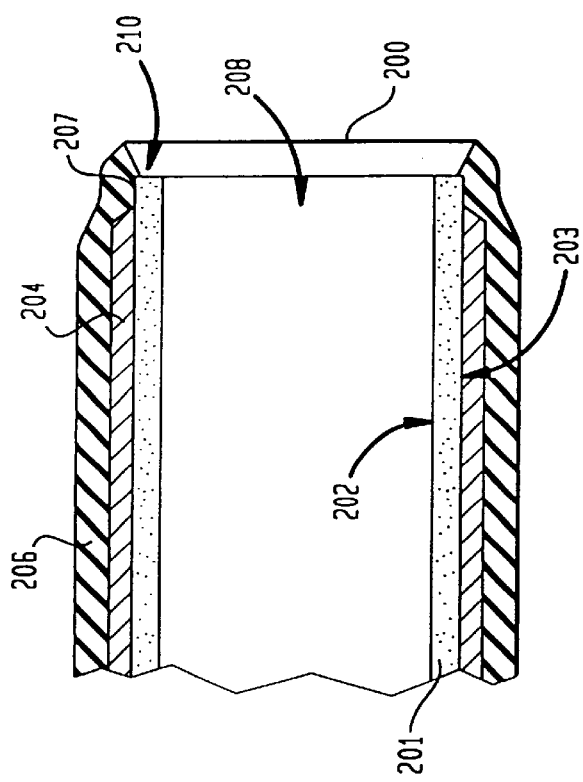

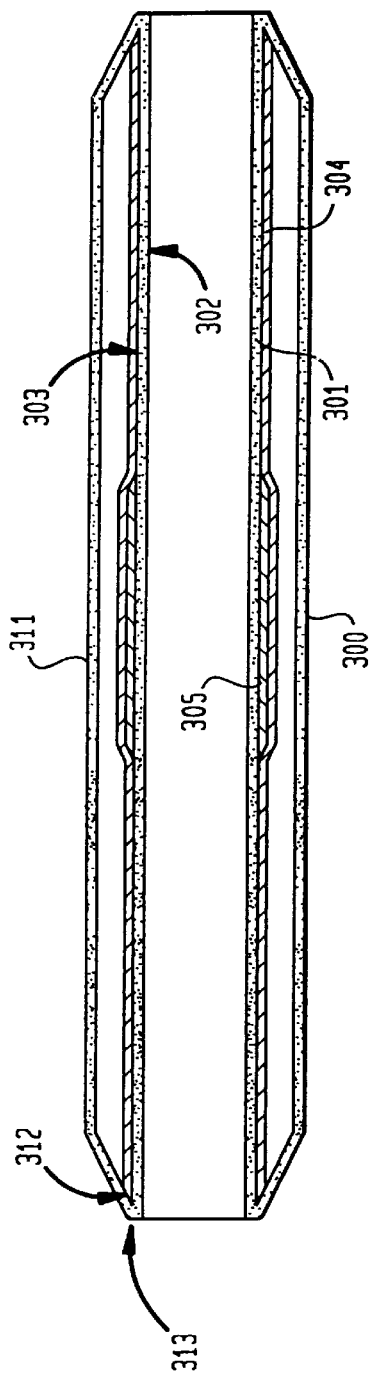
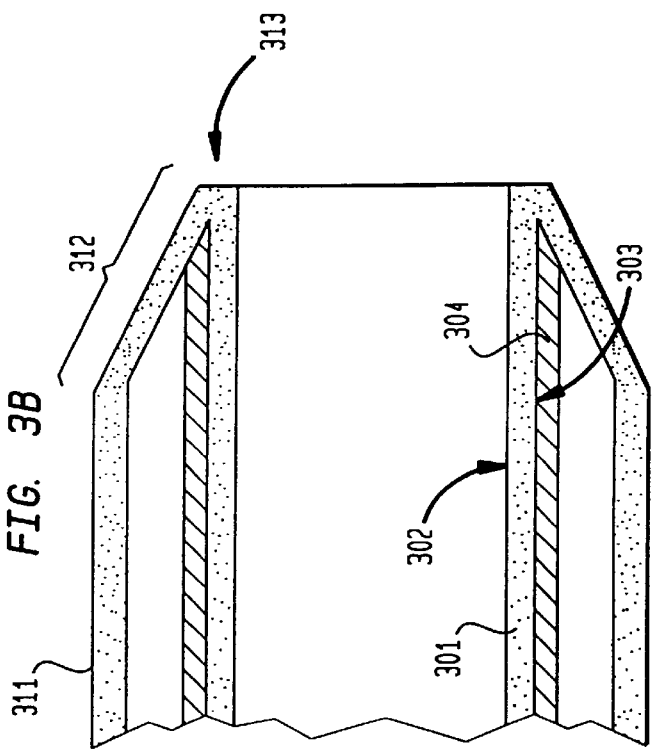

METHOD OF MAKING A HOLLOW-TUBE PRECURSOR BRACHYTHERAPY DEVICE

CROSS REFERENCE TO RELATED APPLICATIONS

This is a Divisional of U.S. patent application Ser. No. 08/903,850, now U.S. Pat. No. 6,163,947 which is a Continuation-in-Part in the nature of a Divisional of U.S. patent application 08/563,050, now U.S. Pat No. 5,713,828 and which is a Continuation pursuant to 35 U.S.C. 365(a) to PCT Application PCT/US96/19109.

BACKGROUND OF THE INVENTION

FIELD OF THE INVENTION

The invention disclosed herein relates to radioactive implants for medical therapeutic purposes, referred to in the art as "radioactive seeds," "seeds," or "sources." The invention relates to seeds for therapeutic radiation treatment of oncological and other medical conditions. More particularly, the invention is directed to a novel radioactive seed for interstitial implantation brachytherapy and also for general brachytherapy treatments. The invention is also directed to methods of making the seeds and methods of using the seeds.

BACKGROUND OF THE INVENTION

The localized treatment of tumors and other medical conditions by the interstitial implantation of radioactive materials is a recognized treatment modality of long standing. Radioactive implants are used to provide radiation therapy in order to reduce or prevent the growth of tumors that cannot be removed by surgical means. Radioactive implants are also used to prevent the growth of microscopic metastatic deposits in lymph nodes that drain the region where a tumor has been removed. Implants are also used to irradiate the postoperative tumor bed after the tumor is excised. Implantation of radioactive sources directly into solid tumors for the destruction of the tumors is used in a therapy referred to as brachytherapy.

Brachytherapy is also used to prevent the regrowth of tissue in circumstances such as the treatment of arteries for occlusive disease. Brachytherapy is applied, for example, in the treatment of atherosclerosis to inhibit restenosis of blood vessels after balloon-angioplasty or other treatments to open occluded or narrowed vessels. These brachytherapy treatments involve a short-term application of extremely radioactive sources. The applications can be for periods as short as a few minutes. This form of brachytherapy may therefore be contrasted with the treatment of tumors where lower activity sources are used for longer periods of time that may be measured in hours or days or may involve permanent implantation.

Treatment of medical conditions with the local application of radiation by implantation concentrates the treatment on the adjacent tissue and advantageously minimizes the exposure of more distant tissues that it is not desired to irradiate. Direct implantation of radioactive sources into tumors often permits the application of larger doses of radiation than may otherwise be achieved because the radiation is applied directly at the site to be irradiated. Local application of brachytherapy to non-cancerous conditions also allows the use of more intensive treatment than is possible by other means.

In the prior art, brachytherapy "sources" are generally implanted for short periods of time and usually are sources of high radiation intensity. For example, irradiation of body cavities such as the uterus has been achieved by placing radium-226 capsules or cesium-137 capsules in the lumen of the organ. In another example, tumors have been treated by the surgical insertion of radium needles or iridium-192 ribbons into the body of the tumor. In yet other instances gold-198 or radon-222 have been used as radioactive sources. These isotopes require careful handling because they emit highly energetic and penetrating radiation that can cause significant exposure to medical personnel and to the normal tissues of the patient undergoing therapy. Therapy with sources of this type requires that hospitals build shielded rooms, provide medical personnel with appropriate protection and establish protocols to manage the radiation hazards.

The prior art interstitial brachytherapy treatment using needles or ribbons has features that inevitably irradiate normal tissues. For example, normal tissue surrounding the tumor is irradiated when a high energy isotope is used even though the radiation dose falls as the square of the distance from the source. Brachytherapy with devices that utilize radium-226, cesium-137 or iridium-192 is hazardous to both the patient and the medical personnel involved because of the high energy of the radioactive emissions. The implanted radioactive objects can only be left in place temporarily; thus the patient must undergo both an implantation and removal procedure. Medical personnel are thus twice exposed to a radiation hazard.

In prior art brachytherapy that uses long-term or permanent implantation, the radioactive device is usually referred to as a "seed." Where the radiation seed is implanted directly into the diseased tissue, this form of therapy is referred to as interstitial brachytherapy. It may be distinguished from intracavitary therapy, where the radiation seed or source is arranged in a suitable applicator to irradiate the walls of a body cavity from the lumen.

Migration of the device away from the site of implantation is a problem sometimes encountered with presently available iodine-125 and palladium-103 permanently implanted brachytherapy devices because no means of affirmatively localizing the device may be available.

The prior art discloses iodine seeds that can be temporarily or permanently implanted. The iodine seeds disclosed in the prior art consist of the radionuclide adsorbed onto a carrier that is enclosed within a welded metal tube. Seeds of this type are relatively small and usually a large number of them are implanted in the human body to achieve a therapeutic effect. Individual seeds of this kind described in the prior art also intrinsically produce an inhomogeneous radiation field due to the form of the construction.

The prior art also discloses sources constructed by enclosing iridium metal in plastic tubing. These sources are then temporarily implanted into accessible tissues for time periods of hours or days. These sources must be removed and, as a consequence, their application is limited to readily accessible body sites.

Prior art seeds typically are formed in a manner that differs from isotope to isotope. The form of the prior art seeds is thus tailored to the particular characteristics of the isotope to be used. Therefore, a particular type of prior art seed provides radiation only in the narrow range of energies available from the particular isotope used.

Brachytherapy seed sources are disclosed in, for example, U.S. Pat. No. 5,405,165 to Carden, U.S. Pat. No. 5,354,257 to Roubin, U.S. Pat. No. 5,342,283 to Good, U.S. Pat. No. 4,891,165 to Suthanthiran, U.S. Pat. No. 4,702,228 to Russell et al, U.S. Pat. No. 4,323,055 to Kubiatowicz and U.S. Pat. No. 3,351,049 to Lawrence, the disclosures of which are incorporated herein by reference.

The brachytherapy seed source disclosed in U.S. Pat. No. 5,405,165 comprises small cylinders or pellets on which palladium-103 compounded with non-radioactive palladium has been applied by electroplating. Addition of palladium to palladium-103 permits electroplating to be achieved and allows adjustment of the total activity of the resulting seed. The pellets are placed inside a titanium tube, both ends of which are sealed. The disclosed invention does not provide means to fix the seed source within the tissues of the patient to ensure that the radiation is correctly delivered. The design of the seed source is such that the source produces an asymmetrical radiation field due to the radioactive material being located only on the pellets. The patent also discloses the use of end caps to seal the tube and the presence of a radiographically detectable marker inside the tube between the pellets.

U.S. Pat. No. 5,354,257 relates to radioactive iridium metal brachytherapy devices positioned at the end of minimally invasive intravascular medical devices for providing radiation treatment in a body cavity. Flexible elongated members are disclosed that can be inserted through catheters to reach sites where radiation treatment is desired to be applied that can be reached via vessels of the body.

U.S. Pat. No. 5,342,238 discloses methods such as sputtering for applying radioactive metals to solid manufactured elements such as microspheres, wires and ribbons. The disclosed methods are also disclosed to apply protective layers and identification layers. Also disclosed are the resulting solid, multilayered, seamless elements that can be implanted individually or combined in intracavitary application devices.

U.S. Pat. No. 4,891,165 to Suthanthiran relates to the production of brachytherapy seed sources and discloses a technique for use in the production of such sources. The patent discloses an encapsulation technique employing two or more interfitting sleeves with closed bottom portions. The open end portion of one sleeve is designed to accept the open end portion of a second slightly-smaller-diameter sleeve. The patent discloses the formation of a sealed source by sliding two sleeves together. Seeds formed by the Suthanthiran process may have a more uniform radiation field than the seed disclosed by U.S. Pat. No. 5,405,165. However, the seed disclosed by Suthanthiran provides no means for securely locating the seed in the tissue of the patient. The U.S. Pat. No. 4,702,228 to Russell et al. relates to the production of brachytherapy seed sources produced by the transmutation of isotopically enriched palladium-102 to palladium-103 by neutrons produced by a nuclear reactor. The Russell patent also discloses a titanium seed with sealed ends, similar to that of Carden, containing a multiplicity of components. A seed produced in this manner is associated with yielding a less than isotropic radiation field.

U.S. Pat. No. 4,323,055 teaches a titanium seed with ends sealed by laser, electron beam or tungsten inert gas welding. The radioactive component of the seed is disclosed to be a silver bar onto which the radioisotope iodine-125 is chemisorbed. Seeds produced in this manner also tend to produce an asymmetric radiation field and provide no means of attachment to the site of application in the patient.

U.S. Pat. No. 3,351,049 discloses a radioactive seed with a titanium or plastic shell with sealed ends. Seeds are disclosed containing a variety of cylindrical or pellet components onto which one of the radioisotopes iodine-125, palladium-103, iridium-192 or cesium-131 is incorporated. The structure of the disclosed seeds yields a non-homogeneous radiation field and provides no means for accurately positioning the seed in the tissue that it is desired to irradiate.

Currently available brachytherapy seeds do not easily lend themselves to association with suture material. For example, iodine-125 seeds currently in use are placed inside suture material at the time of manufacture. However, the insertion process is tedious and time consuming and has the potential for significant radiation exposure to the production personnel involved. Additionally, because of the natural decay of the radioisotope, the suture material thus produced has a short shelf life. As a second example, the manufacturing process used to produce the palladium-103 seeds that are currently in use results in end-roughness of the encapsulation of the seed. The capsules are not placed inside suture material because the end-roughness makes insertion very difficult. Rigid rods are produced in present technology by the insertion of seeds into suture material followed by heat treatment to form a rigid rod containing the seed. These rods are difficult to produce, very fragile and sensitive to moisture. The presently available brachytherapy technology requires that most physicians use suture material preassembled with the seeds already inside. Similarly, rigid materials used by surgeons for brachytherapy are pre-manufactured and purchased readymade.

SUMMARY OF THE INVENTION

The present invention provides a novel general-use brachytherapy device for the interstitial radiotherapy of malignant neoplasms or other diseases treatable with radiation. The device of the instant invention comprises a hollow tubular support with a lumen that is open on both ends. The tubular support of the device bears a radioactive layer that is enclosed with a sealing layer to prevent contact between the radioactive material and the tissues and fluids of the patient.

The hollow tubular support of the present invention comprises a hollow-tube-shaped seed-substrate that has internal and external surfaces. Other embodiments of the instant invention have perforations through the walls of the hollow tube. In embodiments that have perforations through the walls of the tube, the perforations may be oriented in any direction. The various elements of the device may be made of titanium or other biocompatible metal or may be made of synthetic material such as plastic.

The radioactive source material is disposed as a layer on the external surface of the tube of the device. Other materials, such as radiographically detectable material, may also be layered on the external surface of the tube of the device. The entire device is provided with a biologically-compatible, radiation-permeable, surface-sealing layer that entirely seals the external surface of the tube.

An object of the invention disclosed herein is to provide for the improved treatment of medical conditions such as neoplastic diseases according to the normal practice of brachytherapy, e.g., the interstitial implantation of radioactive sources into tumorous tissue for the purpose of irradiating and thus killing malignant cells.

An object of the invention disclosed herein is to provide a brachytherapy device specifically intended to ease the task of surgeons, urologists, radiation therapists, radiologists and others who use brachytherapy devices in providing treatment to patients. The hollow tubular design promotes simple and efficient interaction between the device and suture materials commonly used in surgery. Simply stated, the hollow-tube-shaped form of the device disclosed herein permits suture material, rigid rods or other biocompatible connecting members to be passed through it in such a way as to fix its position relative to the treatment volume. The suture material, rigid rod or other biocompatible connecting member may be threaded through the device at the time of surgery and can also serve to locate the device relative to other similar devices. This flexibility allows a surgeon to effectively react to challenges not revealed by the pre-surgical work-up of the patient.

The design of the invention disclosed herein promotes simple and efficient interaction between the device and suture materials commonly used in surgery. Thus, the brachytherapy device disclosed herein has special application to the form of brachytherapy wherein seeds are associated with flexible suture material and are thereby held in a compliant array in the neoplastic tissue by the suture while their radiation dose is delivered. This greatly speeds and simplifies the process of applying the brachytherapy device, greatly improves the accuracy of emplacement in the tumor and reduces the hazard to which medical personnel are exposed.

The hollow-tube feature of the invention disclosed herein also has special application to the form of brachytherapy in which seeds are associated with a rigid, biocompatible material which holds the seeds in a fixed array in the neoplastic tissue while their radiation dose is delivered. In a similar manner to that described above the disclosed device may be simply threaded onto any commonly used rigid support material to yield a suitable array. For example a hollow-tube brachytherapy device as disclosed herein may be applied by threading a surgical stainless-steel wire or plastic surgical filament through the lumen. The threaded material may then be used to fix the device to the catheter. The catheter is then used to position the array at a site where brachytherapy is needed.

The most preferred overall dimensions of the device disclosed herein may be a diameter of approximately 0.8 mm and a length of approximately 4.5 mm. The advantage of providing a seed in these dimensions is that the device of the present invention may be implanted using currently available instruments. Thus, the need for retooling by the therapist may be avoided, and a brachytherapy device that incorporates the seed-substrate of the instant invention may be applied without modification of current surgical practices. Alternatively, the dimensions of the seed-substrate may be different from those disclosed above, depending upon the specific use to which the device is to be put. Such different dimensions will be apparent to those of skill in the art.

The devices disclosed herein are designed to deliver a therapeutic dose of radiation to a spatially well defined and limited volume of diseased tissue within a living body. Such a device is shaped as a hollow tube so that a suture material, rigid rod or other biocompatible connecting member passed through it can be used to fix its position relative to other similar devices. The threaded connecting member can also serve to locate the device relative to the treatment volume.

The hollow-tube design of the device of the present invention also permits the growth of tissue into the device. This tissue growth acts to anchor the device at the application site and minimize the potential for migration. In embodiments of the device provided with perforations, the perforations also provide additional access for body fluids and tissues to the space inside the tube.

Another object of the invention disclosed herein is to provide an embodiment of the device that has its central tube-shaped substrate formed from a material that is essentially transparent to the radiation emitted by the therapeutic isotope. Such material may be titanium, carbon, stainless-steel, tantalum, hafnium or zirconium. The central tube may also be formed from plastics such as polypropylene, polyethylene terephthalate, nylon, polyurethane, polyphenylene oxide blends, polyphenylsulfone, polysulfone, polyether sulfone, polyphenylene sulfide, phenyletheretherketone, polyetherimide or liquid crystal polymer.

The radioactive material of the embodiments of the invention as disclosed herein is coated on the outer surface of the hollow-tube-shaped seed-substrate and is protected by the sealing layer. Suitable radioisotopes are palladium-103 or iodine-125. Other isotopes that emit radiation with the desired therapeutic properties can also be deposited over the outer surface of the tube in a uniform manner, for example gold-198, yttrium-90 and phosphorus-32. The radioactive material in this layer may already be radioactive when it is applied such as by the application of palladium-103 or iodine-125, or it may be applied as a precursor isotope such as gold-197, yttrium-89, iridium-191 or palladium-102 that can be applied and then transmuted in situ, as disclosed in more detail below.

In yet another embodiment of the instant invention a non-radioactive pre-seed is disclosed. In this embodiment the layer of the device that will be radiation-emitting may be prepared by first plating the hollow-tube-shaped seed-substrate with a suitable non-radioactive isotope that may be transmuted in situ to the desired radiation-emitting isotope by bombardment with neutrons. The material in this layer may be a precursor isotope such as gold-197, yttrium-89, iridium-191 or palladium-102. Upon neutron irradiation gold-197 is transmuted to "gold-198" (which is actually a mixture of gold-198 and gold-199) with a half-life of 2.7 days and with radiation-emitting properties suitable for brachytherapy. For simplicity this isotope produced by this transmutation is referred to hereinafter as "gold-198." Similar processes or transmutation can be used to produce yttrium-90 from yttrium-98 or palladium-103 from palladium-102.

A particular advantage of this technique is that the time and intensity of the neutron irradiation can be adjusted to achieve a particular desired level of activity in the finished device. The technique of neutron irradiation takes advantage of the fact that titanium and some other low-atomic-number metals have small nuclear cross-sections and are essentially unaffected by neutron irradiation. A further advantage of this embodiment of the invention is that no radioactive material is used in the actual manufacturing of the device. A third advantage is that manufactured devices may be stored indefinitely and may be rendered radioactive when needed by exposure to neutron irradiation from a nuclear reactor or cyclotron or other suitable source.

In such an embodiment of the invention, the transmutable non-radioactive isotope is first plated onto the hollow-tube-shaped seed-substrate. Second, the plated hollow-tube seed-substrate is inserted into a closely fitting outer tube of the same length, or slightly longer if the outer tube is to be swaged, that provides the sealing layer. This outer tube can be a metal such as titanium, and is made so that this sealing member or outer tube, fits snugly over the inner tube coated with the radioisotope and radiographically detectable band (if present). The ends of the inner and outer tubes are swaged together and joined, for example by laser welding, so as to form a sealed device. The sealed device thus formed has the form of a double-walled tube. The sealing layer may also be formed from stainless-steel, tantalum, hafnium or zirconium.

Alternatively, the outer tube can also be a synthetic material, such as one of the plastics mentioned above, made so that this sealing member or outer tube fits snugly over the inner tube coated with the radioisotope and radiographically-detectable band (if present). In the case of a plastic sealing member the ends of the inner and outer tubes can be sealed by standard techniques like gluing, heat sealing, solvent bonding or ultrasonic welding.

In yet another embodiment of the sealing layer, a material that is essentially transparent to the radiations emitted by the therapeutic isotope is deposited upon the surface. For example, the sealing layer may be made of a material such as pyrolytic carbon deposited from a chemical vapor or such as titanium deposited from an atomic vapor. The sealing layer may also be formed from carbon, tantalum, hafnium or zirconium, or may be formed from titanium carbide, titanium nitride, titanium carbonitride, hafnium nitride, or zirconium nitride.

Alternatively, in another embodiment of the invention disclosed herein the sealing layer may consist essentially of an organic coating, as for example an organic coating formed from a heat-shrinkable plastic, a coating produced by solvent evaporation, a coating produced by a chemical polymerization reaction or a coating formed by molding plastic around the device. Such organic coatings may be polypropylene, polyethylene terephthalate, nylon, polyurethane, polyphenylene oxide blends, polyphenylsulfone, polysulfone, polyether sulfone, polyphenylene sulfide, phenyletheretherketone, polyetherimide or liquid crystal polymer.

Another feature of the invention disclosed herein provides advantages in situations in which a remote afterloading technique is used. For example, remote afterloading may be used with implants that are temporary implants in the brain. The form of the brachytherapy device disclosed herein offers advantages because isotopes incorporated into these sources (palladium-103 or iodine-125) emit X-rays of average energy between 21 and 30 keV. A consequence of this low energy is to greatly simplify shielding. For example, the half-value thickness (the thickness of lead required to reduce the dose rate from a source to 50%) is only 0.006 mm for palladium-103 and 0.02 mm for iodine-125.

Because the devices disclosed herein are simple to shield, most of the features normally associated with brachytherapy techniques that involve remote afterloading are not applicable. Use of the devices disclosed herein would generally not require remote transfer of the radiation source from a shielded container into the tube implanted in the patient. Similarly, the necessity to isolate the patient in a shielded room during treatment is generally avoided with the disclosed devices. Isotopes incorporated into other embodiments of the device emit beta-particles rather than electromagnetic radiations. These beta-particle emitting embodiments are advantageous in that they may also be effectively shielded by much smaller combinations of plastic and lead than those required by previously available afterloader sources.

Localization of sources following implantation is of importance because accurate knowledge of the position and orientation of the sources can confirm that they are in the positions specified in the medical treatment plan and consequently will provide a properly distributed radiation dose within the treatment volume. To provide means whereby the device can be located after implantation, one embodiment of the present invention is formed with radiographically opaque material such as gold, platinum or other appropriate high-atomic-number element deposited on the device, preferably as a band on the surface near the center of the device. This radiopaque material allows the visualization of the implanted device by standard radiographic procedures and allows the location and orientation to be accurately determined during treatment.

When the radioactive material is applied to an embodiment of the invention that bears a band of radiographically detectable material, the radioactive material may extend over the band of radiographically detectable material. In another embodiment the radioactive material may extend only to within approximately 0.5 mm of the end edge of the tube-shaped seed-substrate and thus provide a narrow non-radioactive ring at each end of the device. Generally, the radioactive material may be disposed on the device to suit many purposes that will be obvious to those of skill in the art.

In preferred embodiments of the present invention, a biocompatible sealing layer is deposited so that the entire external surfaces of the device are composed of a biocompatible material. The sealing layer prevents radioactive materials from escaping and provides a radioactive device which meets the normal definition of a "sealed source." The sealing layer is made of a plastic material or any other biocompatible material, provided the material is adequately transparent to the therapeutic radiation and has sufficient durability to protect and retain the radioisotope underneath. In another embodiment the sealing layer can be made of titanium or other suitable biocompatible metal that is adequately transparent to the therapeutic radiation.

The device disclosed herein will be used for the treatment of medical conditions such as neoplastic diseases according to the normal practice of brachytherapy, e.g., the interstitial implantation of radioactive sources into tumorous tissue for the purpose of irradiating and thus killing malignant cells. Other uses are the emplacement into vessels of the body, e.g., to inhibit restenosis of blood vessels.

BRIEF DESCRIPTION OF THE DRAWINGS

FIG. 2a shows a diagrammatic representation of a cross section of an alternative device of the instant invention formed with a electroplated sealing layer.

FIG. 2b shows a diagrammatic representation of a cross section of the end of the device shown in FIG. 2a to reveal details of the interaction of the electroplated sealing layer and the tube-shaped seed-substrate.

FIG. 3a shows a diagrammatic representation of a cross section of yet another device of the instant invention formed with an outer tube sealing layer.

FIG. 3b shows a diagrammatic representation of a cross section of the end of the device shown in FIG. 3a formed with an outer tube sealing layer to reveal details of the swaged and welded joint.

DETAILED DESCRIPTION OF THE INVENTION

Figure 1A:
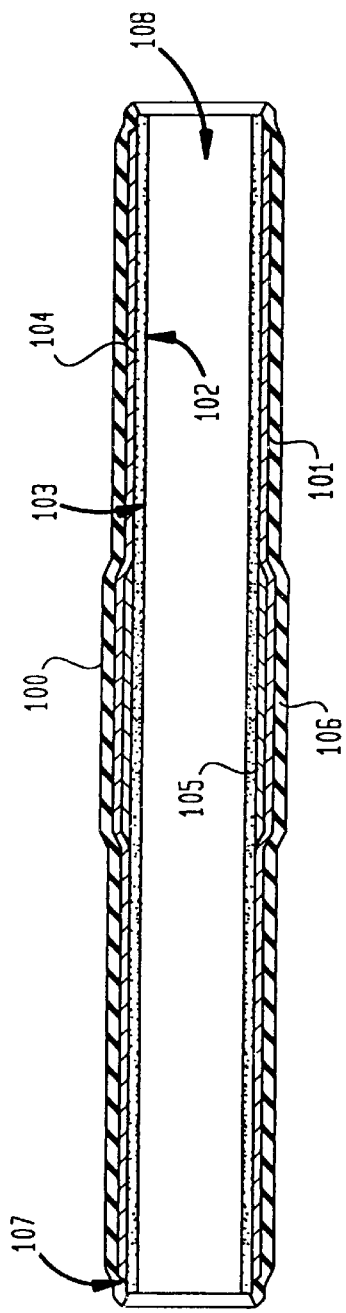
FIG. 1a shows a diagrammatic representation of a cross section of a device of the instant invention that is formed with a plastic sealing layer.

An embodiment of the device disclosed herein that has a radiographically detectable band provides means whereby the device can be located after implantation. Thus, embodiments of the present invention may be formed with a band of a radiographically-detectable material such as gold, platinum or another appropriate high-atomic-number element deposited near the center on the external surface of the hollow-tube-shaped seed-substrate. This band allows the visualization of the implanted device by standard radiographic procedures and allows the location and orientation to be accurately determined during treatment or in advance of surgery. The radiographically detectable band may be applied to entirely encircle the external surface of the hollow-tube-shaped seed-substrate at right-angles to the longitudinal axis of the seed. The band may be 1.2 mm wide and be centrally positioned to allow accurate determination of the position of the seed by standard radiographic, fluoroscopic or computer-tomography visualization. The band of radio-detectable material such as gold, platinum or another appropriate high-atomic-number element may be deposited by means similar to those described below for deposition of the radioactive source material.

In manufacturing one embodiment of the invention disclosed herein, a therapeutic radioisotope is deposited on the outward-facing surface of the hollow-tube-shaped seed-substrate in such a manner as to produce an essentially uniform cylindrical radiation field in close proximity to the device. The radioactive layer is then covered by a sealing layer, the purpose of which is to prevent the escape of a significant amount of the radioactive material into the surrounding living body.

The disposition of the radioactive source layer on the external surface of the hollow-tube-shaped seed-substrate may be varied to achieve different ends. As example, the radioactive source layer may extend over the entire external surface of the hollow-tube-shaped seed-substrate and extend over a previously-applied radiographically detectable band. In an alternative embodiment the radioactive source layer may be excluded from a region at each end of the external surface of the hollow-tube-shaped seed-substrate in order to provide a narrow non-radioactive ring at each end of the seed. In a further embodiment, the radioactive source layer may extend over the entire external surface of the hollow-tube-shaped seed-substrate with the exception of the region that bears the radiographically detectable band.

An embodiment of the invention disclosed herein may have the central hollow-tube-shaped seed-substrate formed from a material essentially transparent to the radiation emitted by the therapeutic isotope. Such materials may be elements such as titanium, carbon, tantalum, hafnium or zirconium or an alloy such as stainless-steel. Alternatively, organic polymers may be used for fabrication of the hollow-tube-shaped seed-substrate and may be any of a number of materials such as polypropylene, polyethylene terephthalate, nylon, polyurethane, polyphenylene oxide blends, polyphenylsulfone, polysulfone, polyether sulfone, polyphenylene sulfide, phenyletheretherketone, polyetherimide or liquid crystal polymers. Such polymers and their sources are disclosed in Table 1.

A further feature of embodiments of the invention is that the radioactive layer is covered by a sealing layer, the purpose of which is to prevent contact with the radioactive isotope and to prevent the escape of radioactive material into the surrounding living body.

The sealing layer may be a material essentially transparent to the radiation emitted by the therapeutic isotope, such as pyrolytic carbon deposited from a chemical vapor. An alternative sealing layer such as titanium may be deposited from an atomic vapor. A further embodiment of the sealing layer may comprise an organic coating, as for example a coating formed from a heat shrinkable plastic, a coating produced by solvent evaporation, a coating produced by a polymerization reaction or by molding plastic around the exterior of the device.

An optional feature of the invention disclosed herein is to provide a radiographically detectable band, desirably applied near the median point of the long axis of the device with sufficient width and opacity to make the device visible and its orientation apparent on a radiograph taken of a patient following implantation of the device.

The lumen of the hollow-tube-shaped seed-substrate comprises a substantial proportion of the total diameter of the device. In a preferred embodiment, the total wall thickness of the seed including the inner tube substrate, radioisotope source material layer, radiographically-detectable band if present and sealing layer is approximately 0.15 mm, and the lumen diameter is approximately 0.51 mm, large enough to admit the passage through it of suturing needles and sutures.

TABLE 1

ACCEPTABLE NONABSORBABLE POLYMERS WITH THEIR TRADE NAMES AND COMMERCIAL SOURCES

| Material | Trade Names | Sources |
| --- | --- | --- |
| Polyurethane | Texin, Desmopan, Estane | Bayer Corp., B F Goodrich |
| Polypropylene | Surgilene, Prolene | Ethicon, American Cyanamid |
| Polyethylene terephthalate (PET) | Impet, Petra, Rynite, Estar | Allied, Hoechst, Celanese, duPont, Eastman |
| Polyphenylene oxide blends (PPO) | Noryl, Prevex | General Electric |
| Polyphenylsulfone (PPSU) | Radel R | Amoco |
| Polysulfone (PSU) | Udel, Ultrason S | Amoco, BASF |
| Polyether sulfone (PES) | Radel A, Ultrason E | Amoco, BASF |
| Polyphenylene sulfide (PPS) | Fortron, Ryton, Supec | Hoechst, Celanese, Phillips, GE |
| Phenyletheretherketone (PEEK) | Kadel, Victrex | Amoco, Victrex |
| Polyetherimide (PEI) | Ultem | GE |
| Nylon | Nylon | duPont |
| Liquid crystal polymer (LCP) | Vectra | Hoechst, Celanese |

In other embodiments of the instant invention, the wall of the hollow-tube-shaped seed-substrate may be pierced transversely by one or more perforations. In embodiments that have perforations through the wall of the tube, the perforations may be shaped and oriented in any direction in order to best serve the purposes disclosed below. In embodiments of the device that are provided with perforations, the perforations provide access for body fluids to the lumen of the tube. Perforations in the wall of the tube may also provide anchor points as tissue grows into the holes. Perforations may desirably be in the range of 0.031 to 0.31 mm wide.

The hollow-tube-shaped seed-substrate of the instant invention may be made of titanium or other biocompatible metal or may be made of synthetic material such as plastic. Where titanium or other biocompatible metal is used, the tubes may be formed by standard cold-drawing processes to form metal tubes. For example, hollow-tube-shaped seed-substrates of the instant invention may be made from ASTM B265-78 grade 2 titanium by forming tubular sections 4.5 mm in length, 0.57 mm in outside diameter and 0.5 mm inside diameter. Such titanium tubes are available commercially in the U.S.A. from the Uniform Tube Company, Collegeville, Pa. 19426.

Where the hollow-tube-shaped seed-substrate of the instant invention is made of plastic or synthetic material, the seed-substrate may be formed by extruding or molding the tube from the mass material in a manner suitable to the material being formed. A number of engineering plastics represent acceptable materials including polypropylene, polyetherimide, polyethylene terephthalate, nylon, polyurethane, polyphenylene oxide blends, polyphenylsulfone, polysulfone, polyether sulfone, polyphenylene sulfide, phenyletheretherketone, polyetherimide or liquid crystal polymers. These materials are available from suppliers listed in Table 1. Other polymeric and plastic materials that are suitable for use in the present invention will be obvious to those skilled in the art.

The radioactive source material of the instant invention is disposed as a layer on the external surface of the hollow-tube-shaped seed-substrate. The instant invention differs in this respect from prior art brachytherapy devices. In the prior art, brachytherapy devices are generally disclosed in which the radioactive source material is present in association with a pellet or rod contained within an encapsulating chamber. The structure of the instant invention is advantageous in that all components of the source, including the disposition of the radioactive source material and a radiographically detectable band, if present, are deposited onto the external surface of the structural member of the seed, the hollow-tube-shaped seed-substrate. The central lumen of the seed-substrate is unobstructed, thus making the hollow design possible with all the subsequent advantages imparted by that design.

Designers of prior art brachytherapy devices made use of internal components such as pellets or rods to provide a support for the radioactive source material of the seed. In some prior art designs, radiographically-detectable markers were also encapsulated together with the radioactive source material. The use of such internal components in prior art designs requires an encapsulating chamber and precludes a hollow-tube-shaped seed design.

The radioactive source layer is applied to the hollow-tube-shaped seed-substrate by any of a variety of conventional process such as sputtering, laser ablation, cathodic arc plasma deposition, curvilinear cathodic arc plasma deposition, vapor deposition, or electroplating. Such known processes are further set forth in U.S. Pat. No. 5,342,238 to Good, the disclosure of which is hereby incorporated by reference.

For example, but not by way of limitation, the radioactive layer on the hollow-tube-shaped seed-substrate may be electroplated onto the external surface of the hollow-tube-shaped seed-substrate. The exact method for application of the layer depends upon the material to be deposited and the material of which the tube is constructed. If the tube is constructed from a material which does not conduct electricity, such as a plastic, the outer surface must first be metallized to make it conducting. This may be achieved by any one of several standard techniques commonly used in the plastics industry. If the tube is constructed from a material difficult to electroplate, such as titanium, a surface pretreatment is required to obtain reliably-adherent electrodeposition of plating layers.

For example, a surface pretreatment procedure for titanium has been disclosed by Pratt Whitney Aviation that includes an abrasive blast, a hot alkaline cleansing in 30% potassium hydroxide, a hydrochloric acid pickle, a "bright dip" (achieved by dipping in an aqueous solution of 12% by volume acetic acid, 70% hydrofluoric acid and 1% nitric acid), an "anodic etch" for 6 minutes at 162 amperes per square meter (achieved in 13% by volume hydrofluoric acid, 83% acetic acid and 4% water), a "sulfate nickel strike" to an approximate thickness of 25 microinches followed by drying in air for 2 hours at 48 degrees C. This process achieves deposition of a thin nickel layer onto the surface of the titanium, thus providing a more advantageous surface layer for electroplating.

If desired, a radiographically detectable band, for example a band of gold approximately 0.01 mm thick by 1.2 mm wide, deposited from a commercial electroplating solution (for example AuRoTechP1 from AT&T Electroplating Chemicals and Services) can be deposited directly onto a previously-applied thin nickel layer applied as described above.

Embodiments of the instant invention may incorporate different therapeutic isotopes in order to achieve different therapeutic purposes and to achieve different activities. For example, beta-particle emitting isotopes such as yttrium-90 and phosphorus-32 may be prepared with total activities of from 0.1 to 100 millicuries. Beta-emitting devices are anticipated to be used for therapy where relatively little penetration of the radioactivity is desired. In other embodiments isotopes that emit electromagnetic radiation are used. Such embodiments may have activities as high as 10 curies and are used in applications such as short-term applications of only a few minutes to prevent or inhibit the restenosis of blood vessels after angioplasty.

If the therapeutic radioisotope is palladium-103, the radioactive source material layer may be deposited onto the hollow-tube-shaped seed-substrate by the method disclosed in U.S. Pat. No. 5,405,309 to Carden, the disclosure of which is hereby incorporated by reference. This electroplating technology can provide apparent activities of from 0.1 to 300 millicuries per seed.

If the therapeutic radioisotope to be used is iodine-125, a uniform layer of silver is first deposited onto the outer surface of the hollow-tube-shaped seed-substrate. Any of the techniques cited above can be used for this purpose provided a uniform and adherent layer of approximately 0.025 mm thickness results. The iodine-125 is then chemisorbed onto the silver layer by the method disclosed in U.S. Pat. No. 4,323,055 to Kubiatowicz, the disclosure of which is hereby incorporated by reference. This procedure can provide apparent seed activities of from 0.1 to 100 millicuries per seed.

The radioactive material layer may be deposited in a radioactive form such as the application of palladium-103, iodine-125 or yttrium-90. Alternatively, a precursor isotope such as gold-197, yttrium-89, iridium-191 or palladium-102 may be deposited and then transmuted in situ, for example, by bombardment with neutrons, into the desired therapeutic isotope. For example, yttrium-89 may be deposited on the outer surface of the hollow-tube-shaped seed-substrate by electroplating or otherwise depositing the yttrium-89, and yttrium-90 may be produced by bombardment with neutrons to transmute the non-radioactive isotope. Gold-198 (generally referred to by this designation, though containing gold-199 isotope as well), yttrium-90 and palladium-103 may be produced by analogous processes.

The application of brachytherapy sources for the medical therapeutic application of radiation requires that the radioactive source be entirely sealed to prevent escape of the radioisotope. This is essential to preclude the systemic distribution of the isotope within the patient and contamination of medical personnel, medical facilities and the general environment. In the preferred embodiments of the instant invention, the entire radioisotope source layer is provided with a biologically-compatible, radiation-permeable, surface-sealing layer that entirely seals the external surface of the hollow-tube-shaped seed-substrate with the radioactive and radiographically detectable layers applied thereon. The sealing layer seals to the ends of the hollow-tube-shaped seed-substrate ensuring a hermetic seal. The sealing layer prevents radioactive materials from escaping and provides a radioactive device which meets the normal definition of a "sealed source."

In one embodiment the sealing layer may be made of a plastic material or any other biocompatible organic material, provided the material is adequately transparent to the therapeutic radiation and has sufficient durability to protect and retain the radioisotope. Such a sealing layer will cover the entire external surface and the layers applied thereon of the hollow-tube-shaped seed-substrate. Such a sealing layer may be made from a heat shrinkable plastic, or from a coating formed by solvent evaporation or polymerization reaction, or by molding plastic around the exterior of the device. The adjacent ends of the outer sealing layer and the hollow-tube seed-substrate are joined by the process of applying the sealing layer.

In another embodiment the sealing layer may be made of a plastic material or any other biocompatible organic material, provided the material is adequately transparent to the therapeutic radiation and has sufficient durability to protect and retain the radioisotope. Such a sealing layer will have the form of an outer tube that covers the entire external surface and the layers applied thereon of the hollow-tube-shaped seed-substrate. Such a sealing layer may be made from any of a number of plastics shown in Table 1. The adjacent ends of the outer sealing tube and the hollowtube seed-substrate may be joined by one of several processes. For example they may be joined by gluing, heat sealing, ultrasonic welding or solvent welding.

Manufactured devices are tested for physical integrity and leakage, following the appropriate standard as for example, ANSI-44.2 1973, ANSI-542 1977 and/or ISO-2919. These test standards ensure that devices comply with the requirements to be defined as sealed sources by testing for physical integrity and leakage.

In another embodiment the sealing layer can be made of titanium; hafnium or zirconium metal or other suitable biocompatible metal that is adequately transparent to the therapeutic radiation. Such a sealing layer will seal to the ends of the hollow-tube-shaped seed-substrate and cover the entire external surface and the layers applied thereon of the hollow-tube-shaped seed-substrate. This sealing layer may be applied as a hollow tube which is swaged and bonded on each end of the hollow tube seed substrate. In an alternative embodiment, the sealing layer may be applied as a layer of metal deposited by any of the means cited above to form the radioactive layer.

In yet another embodiment the sealing layer can be made of a layer of titanium carbide, titanium nitride, titanium carbonitride, hafnium nitride, or zirconium nitride as disclosed by Good, or be made of another suitable biocompatible metal or metal compound that is adequately transparent to the therapeutic radiation. Such a sealing layer will cover the entire external surface and the layers applied thereon and seal to the ends of the hollow-tube-shaped seed-substrate or the internal surface of the hollow-tube-shaped seed-substrate in a manner that suffices to meet the objectives of the instant invention.

Figure 1B:
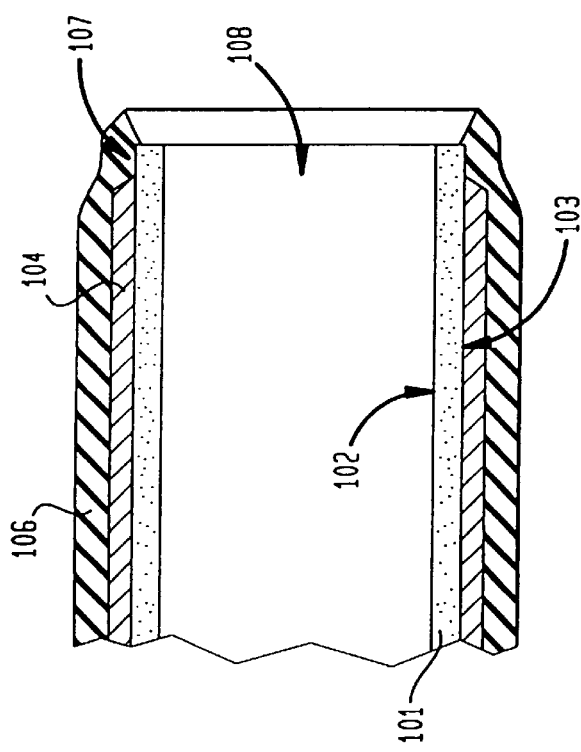
FIG. 1b shows a diagrammatic representation of a cross section of the end of the device shown in FIG. 1a to reveal details of the interaction of the plastic sealing layer and the tube-shaped seed-substrate.

A detailed description of a particular embodiment of the instant invention is made by reference to FIGS. 1a and 1b. The embodiment of the instant invention disclosed in FIG. 1a comprises a novel brachytherapy seed-substrate that has the form of a hollow tube open on both ends and having an internal surface 102 and external surface 103. The hollow-tube-shaped seed-substrate 101 of the device 100 may be made of titanium or other biocompatible metal or may be made of synthetic material such as plastic. The radioactive source material 104 is disposed as a uniform layer on the external surface 103 of the device. The radioactive layer 104 thus has the form of a cylinder disposed upon the external surface 103 of the hollow-tube-shaped seed-substrate 101. A radiographically detectable layer 105 is shown layered on a portion of the external surface 103 of the hollow-tube-shaped seed-substrate. The radiographically detectable layer 105 is thus similarly in the form of a cylinder on the external surface 103 of the hollow-tube-shaped seed-substrate 101 disposed at right-angles to the long axis of the seed-substrate. The entire device 100 is provided with a biologically-compatible, radiation-permeable, surface-sealing layer 106 that entirely covers and seals the radioactive layer 104, the radiographically detectable layer 105 and the ends of the hollow-tube-shaped seed device. The biologically-compatible, radiation-permeable, surface-sealing layer 106 is applied by a process such as shrink-wrapping and forms a seal 107 to the hollow-tube-shaped seed-substrate 101. The lumen of the device 108 is shown.

FIG. 1b shows the details of the hollow-tube-shaped seed-substrate 101 open at an end and having an internal surface 102 and an external surface 103. The radioactive layer 104 is shown as a uniform layer on the external surface 103 of the device 100. The device 100 is provided with a biologically-compatible, radiation-permeable, surface-sealing layer 106 that entirely covers and seals the radioactive layer 104 and the end of the device 100. The biologically-compatible, radiation-permeable, surface-sealing layer 106 is applied by a process such as shrink-wrapping and forms a seal 107 to the tube-shaped seed-substrate 101. The lumen of the device 108 is shown.

FIGS. 2a and 2b show a diagrammatic representation of a cross-section of an embodiment of the instant invention that is formed with a perforation 209 through the wall of the device 200 and is sealed with an electroplated sealing layer 206. The cross-section shows a portion of the hollow-tube-shaped seed-substrate 201 and its internal surface 202 and its external surface 203. The diagram shows the location of the radioactive layer 204 upon the external surface 203 of the hollow-tube-shaped seed-substrate 210 and the radiographically detectable layer 205 also disposed upon the external surface 203 of the hollow-tube-shaped seed-substrate 201. The radioactive layer 204 is excluded from the terminal portion 207 of the external surface 203 of the hollow-tube-shaped seed-substrate 201. The diagram shows the sealing-layer 206 covering the radioactive layer 204, the radiographically detectable layer 205 and the external surface 203 of the hollow-tube-shaped seed-substrate 201. The seal 207 between the electroplated sealing layer 206 and the end 210 of the hollow-tube-shaped seed-substrate 201 is shown.

FIG. 2b shows a diagrammatic representation of the detail of a cross-section of an end of a device 200 of the instant invention that is formed with a electroplated sealing layer 206. The cross-section shows a portion of the hollow-tubeshaped seed-substrate 201 and its internal surface 202 and its external surface 203. The diagram shows the location of the radioactive layer 204 upon the external surface 203 of the hollow-tube-shaped seed-substrate 201. The diagram shows the sealing-layer 206 covering the radioactive layer 204. The end 207 of the hollow-tube-shaped seed-substrate 201 from which the radioactive layer 204 is excluded is shown, together with the seal 210 between the sealing layer 206 and the end 207 of the hollow-tube-shaped seed-substrate 201.

A novel feature of an embodiment of the brachytherapy device disclosed herein is the external tube that is swaged and laser welded to the hollow-tube-shaped seed-substrate shown in FIGS. 3a and 3b. In FIG. 3a a diagrammatic cross section of a complete hollow-tube device 300 with an external sealing tube 311 is shown. The cross-section shows the hollow-tube-shaped seed-substrate 301, its internal surface 302 and its external surface 303. The diagram shows the location of the radioactive layer 304 upon the external surface 303, the location of the hollow-tube-shaped seed-substrate 301 and that of the radiographically detectable layer 305 also disposed upon the external surface 303 of the hollow-tube device 300. The diagram shows the outer sealing-layer 311 enclosing the radioactive layer 304 and the radiographically detectable layer 305. The end of the hollow-tube device 300 showing the swaged region 312 and laser-welded region 313 is shown.

FIG. 3b is a diagrammatic representation of a cross-section of the swaged and laser welded end of double-walled tube device shown in FIG. 3a. The cross-section shows the end of the tube-shaped seed-substrate 301 and its internal surface 302 and its external surface 303. The diagram also shows the location of the radioactive layer 304 upon the external surface 303 of the hollow-tube-shaped seed-substrate 301. The outer sealing-layer 311 is shown enclosing the radioactive layer 304. The swaged region 312 and the laser-welded region 312 at the end of the sealed device is shown.

Figure 4:
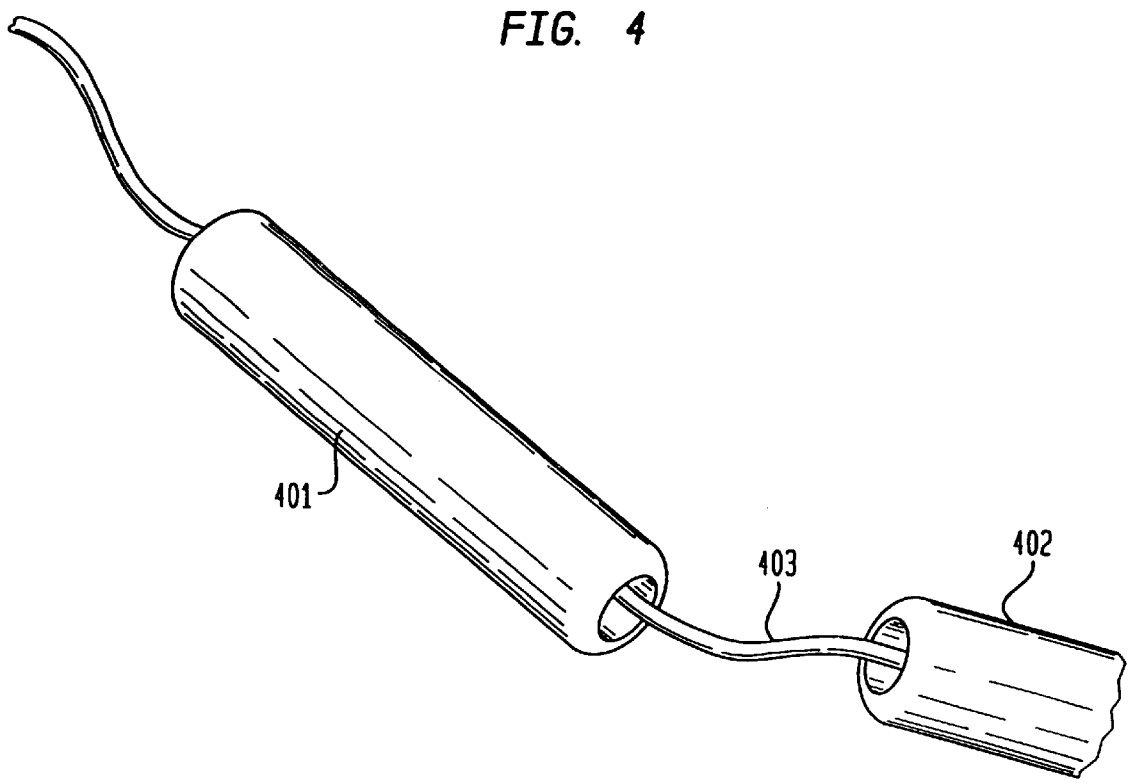
FIG. 4 shows a perspective representation of devices of the instant invention disposed upon a surgical suture.

A particular utility of the hollow-tube-shaped brachytherapy device disclosed herein is its ability to be surgically sewn into position by sutures or rigid elements passed through the lumen of the device. FIG. 4 shows a perspective representation of a device 401 and a portion of a second device 402 of this invention disposed on a suture 403.

Figure 5:
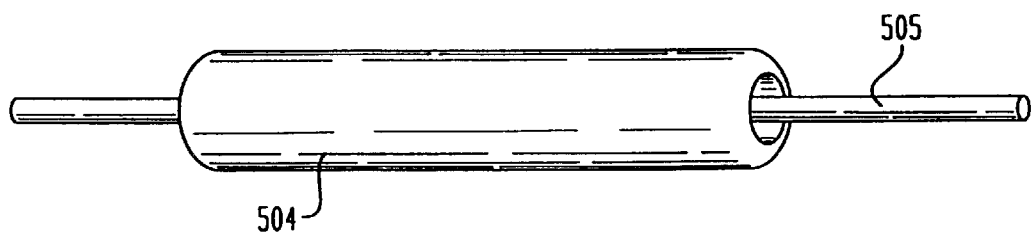
FIG. 5 disposed shows a perspective representation of devices of the instant invention disposed on a rigid surgical support.

FIG. 5 shows a view of a device of this invention 504 shown disposed on a rigid surgical support 505 as the device would be used in practice.

What is claimed is:

1. A method of making a sealed double-walled tubular precursor device adapted to be transmuted into a brachytherapy device and having a lumen therethrough for interstitial implantation of radiation-emitting material within a living body, said method comprising:

depositing a layer of isotope on an external surface of an inner tubular element, said inner tubular element having a first open end, a second open end, and a lumen continuous with said first open end and said second open end;

positioning said inner tubular element within an outer tubular element, said outer tubular element having a first open end, a second open end, and a lumen continuous with said first open end of the outer tubular element and said second open end of the outer tubular element, said inner tubular element being of substantially equal length to said outer tubular element, wherein said inner tubular element is disposed substantially centrally within said outer tubular element and spaced apart therefrom; and sealingly joining said first open end of said inner tubular element and said first open end of said outer tubular element, and sealingly joining said second open end of said inner tubular element and said second open end of said outer tubular element so at to form said sealed double-walled tubular precursor device.

2. The method of claim 1, wherein said inner tubular element comprises at least one of the following materials: titanium, carbon, stainless-steel, tantalum, hafnium and zirconium.

3. The method of claim 1, wherein said isotope comprises at least one of the following materials: palladium-102, iridium-191, gold-197, yttrium-89 and phosphorus-31.

4. The method of claim 1, wherein said isotope is disposed as an essentially uniform layer of isotope.

5. The method of claim 1, wherein said outer tubular element comprises at least one of the following materials: titanium, carbon, stainless-steel, tantalum, hafnium, zirconium, titanium carbide, titanium nitride, titanium carbonitride, hafnium nitride, and zirconium nitride.

6. The method of claim 1, wherein sealingly joining said first open end of said inner tubular element and said first open end of said outer tubular element, and sealingly joining said second open end of said inner tubular element and said second open end of said outer tubular element comprises swaging said ends together, and further sealingly joining said ends by laser welding, so as to form a sealed device.

7. The method of claim 1, wherein said depositing a layer of isotope is achieved by a process of chemoactivation, sputtering, vapor deposition plating, chemical-vapor deposition plating, electroplating or electroless plating.

8. The method of claim 1, additionally comprising:

depositing a radiographically detectable band on a portion of said external surface of said inner tubular element by a process of chemoactivation, sputtering, vapor deposition plating, chemical-vapor deposition plating, electroplating or electroless plating.

9. A method for converting a sealed double-walled tubular precursor device having a lumen therethrough for interstitial implantation of radiation-emitting material within a living body, into a sealed double-walled tubular brachytherapy device, said method comprising:

depositing a layer of isotope on an external surface of an inner tubular element, said inner tubular element having a first open end, a second open end, and a lumen continuous with said first open end and said second open end;

positioning said inner tubular element within an outer tubular element, said outer tubular element having a first open end, a second open end, and a lumen continuous with said first open end of the outer tubular element and said second open end of the outer tubular element, said inner tubular element being of substantially equal length to said outer tubular element, wherein said inner tubular element is disposed substantially centrally within said outer tubular element and spaced apart therefrom; and sealingly joining said first open end of said inner tubular element and said first open end of said outer tubular element, and sealingly joining said second open end of said inner tubular element and said second open end of said outer tubular element so at to form said sealed double-walled tubular precursor device; and irradiating said sealed double-walled tubular precursor device with neutrons so as to transmute said isotope to a radiation-emitting isotope, said neutrons being applied to said sealed double-walled tubular precursor device by a nuclear reactor or a cyclotron.

10. The method of claim 9, wherein said outer tubular element comprises a material essentially transparent to radiations emitted by said radiation-emitting isotope of said sealed double-walled tubular brachytherapy device.

11. A method of making a sealed double-walled tubular precursor device adapted to be transmuted into a brachytherapy device having a lumen therethrough for interstitial implantation of radiation-emitting material within a living body, said method comprising:

fabricating an inner tubular element, said inner tubular element being fabricated to have an external surface, a lumenal surface, a first open end, a second open end, and a lumen continuous with said first open end and said second open end;

fabricating an outer tubular element, said outer tubular element being fabricated to have a first open end, a second open end, and a lumen continuous with said first open end of the outer tubular element and said second open end of the outer tubular element, said tubular element also being fabricated to be of substantially equal length to said tubular support and of a diameter sufficient to permit said tubular support to be positioned within said lumen of said tubular element;

depositing a layer of isotope on said external surface of said inner tubular element;

positioning said inner tubular element within said outer tubular element so that said inner tubular element is disposed coaxially and substantially centrally within said outer tubular element and spaced apart therefrom;

sealingly joining said first open end of said inner tubular element and said first open end of said outer tubular element; and sealingly joining said second open end of said inner tubular element and said second open end of said outer tubular element.

12. The method of claim 11, wherein said inner tubular element comprises at least one of the following materials: titanium, carbon, stainless-steel, tantalum, hafnium and zirconium.

13. The method of claim 11, wherein said isotope comprises at least one of the following materials: palladium-102, iridium-191, gold-197, yttrium-89 and phosphorus-31.

14. The method of claim 11, wherein said isotope is disposed as an essentially uniform layer of isotope.

15. The method of claim 11, wherein said outer tubular element comprises at least one of the following materials: titanium, carbon, stainless-steel, tantalum, hafnium, zirconium, titanium carbide, titanium nitride, titanium carbonitride, hafnium nitride, and zirconium nitride.

16. The method of claim 11, wherein sealingly joining said first open end of said inner tubular element and said first open end of said outer tubular element, and sealingly joining said second open end of said inner tubular element and said second open end of said outer tubular element comprises swaging said ends together, and further sealingly joining said ends by laser welding, so as to form a sealed device.

17. The method of claim 11, wherein said depositing a layer of isotope is achieved by a process of chemoactivation, sputtering, vapor deposition plating, chemical-vapor deposition plating, electroplating or electroless plating.

18. A method for converting a sealed double-walled tubular precursor device having a lumen therethrough for interstitial implantation of radiation-emitting material within a living body, into a sealed double-walled tubular brachytherapy device, said method comprising:

fabricating an inner tubular element, said inner tubular element being fabricated to have an external surface, a lumenal surface, a first open end, a second open end, and a lumen continuous with said first open end and said second open end;

fabricating an outer tubular element, said outer tubular element being fabricated to have a first open end, a second open end, and a lumen continuous with said first open end of the outer tubular element and said second open end of the outer tubular element, said tubular element also being fabricated to be of substantially equal length to said tubular support and of a diameter sufficient to permit said tubular support to be positioned within said lumen of said tubular element;

depositing a layer of isotope on said external surface of said inner tubular element;

positioning said inner tubular element within said outer tubular element so that said inner tubular element is disposed coaxially and substantially centrally within said outer tubular element and spaced apart therefrom;

sealingly joining said first open end of said inner tubular element and said first open end of said outer tubular element;

sealingly joining said second open end of said inner tubular element and said second open end of said outer tubular element; and irradiating said sealed double-walled tubular precursor device with neutrons so as to transmute said isotope to a radiation-emitting isotope, said neutrons being applied to said sealed double-walled tubular precursor device by a nuclear reactor or a cyclotron.

19. The method of claim 18, wherein said outer tubular element comprises a material essentially transparent to radiations emitted by said radiation-emitting isotope of said sealed double-walled tubular brachytherapy device.

* * * * *